US00PP12914P2

(12) United States Plant Patent
Lemon

(10) Patent No.: US PP12,914 P2
(45) Date of Patent: Sep. 3, 2002

(54) VARIETY OF GERANIUM NAMED 'SOPHIA'

(75) Inventor: David G. Lemon, Santa Barbara County, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/478,596

(22) Filed: Jan. 6, 2000

(51) Int. Cl.[7] ..... A01H 5/00
(52) U.S. Cl. ..... Plt./329
(58) Field of Search ..... Plt./329

*Primary Examiner*—Bruce R. Campell
*Assistant Examiner*—Annette H. Para
(74) *Attorney, Agent, or Firm*—Webb Ziesenheim Logsdon Orkin & Hanson, P.C.

(57) ABSTRACT

A new and distinct variety of geranium with improved floret form, improved leaf form, and a more uniform habit than the current variety 'Marilyn'. This variety creates a uniform mound form with clean pink flowers which can be used in hanging baskets, containers or ground beds.

1 Drawing Sheet

BACKGROUND OF THE INVENTION

This discovery relates to a new and distinct cultivar of geranium identified by the name of 'Sophia', Breeder No. 4DG763 and Oglevee, Ltd. No. 5017. The new variety was discovered in a selective breeding program at Oglevee, Ltd. in Connellsville, Pa. The new variety was first asexually reproduced by tip cuttings on Jan. 23, 1995, in Connellsville, Pa. and has been found to retain its distinctive characteristics through successive generations by cuttings. The seed parent to this new cultivar is a seedling floribunda white (Breeder No. 4DG185) (unpatented), and the pollen parent is the cultivar "Aurora" (unpatented).

The new cultivar, when grown in a glass greenhouse in Connellsville, Pa. using full light, 60° F. night temperature, 68° F. day temperature and grown in a soilless media with constant fertilizer at 200–250 ppm nitrogen and potassium, full light, has a response time from a rooted cutting to a flowering plant in a 10 cm pot flowered of six weeks.

DESCRIPTION OF THE DRAWING

The accompanying photographic drawing illustrates the new cultivar at 6 weeks from a rooted cutting, with the color being as nearly true as is possible with color illustrations of this type.

DESCRIPTION OF THE PLANT

The following detailed descriptions set forth the characteristics of the new cultivar. The data which define these characteristics were collected from asexual reproductions carried out at Oglevee, Ltd., 152 Oglevee Lane, Connellsville, Pa. 15425. The color readings on a plant grown in a 20 cm pot were taken indoors under 200–220 foot candles of cool white fluorescent light. Color references are to The R.H.S. Colour Chart of The Royal Horticultural Society of London and common color names.

THE PLANT

Classification:
*Botanical.*—*Pelargonium xhortorum.*
*Commercial.*—Zonal geranium named 'Sophia'.
Form: Free basal branching; uniform mound habit.

Height: 22.0–24.0 cm from media surface.
Growth: Self branching, with some cascading growth.
Strength: Free and early flowering, no mechanical pinching required, free standing, multi-purpose use.
Foliage: Slight zone present.
Leaves:
*Size.*—5.5–7.0 cm across.
*Shape.*—Reinform; cordate base.
*Margin.*—Crenately lobed.
*Texture.*—Leatherly, pubescent.
*Arrangement.*—Alternate, occasionally opposite.
*Color.*—Top: Green Group 143A. Bottom: Green Group 138B. Zone: Yellow-Green Group 147A.
*Ribs and veins.*—Venation: Palmate.
Color: —Yellow-Green Group 144D.
Petioles:
*Length.*—4.0–6.0 cm.
*Color.*—Yellow-Green Group 144A.
*Texture.*—Pubescent.
Stem:
*Color.*—Yellow-Green Group 144A.
*Internode length.*—1.8–2.0 cm.
*Texture.*—Pubescent.

THE BUD

Shape of cluster: Elliptical.
Size:
*Umbel.*—2.0–3.0 cm across when just showing color.
*Bud.*—7.0–8.0 mm long, 3.0–4.0 mm wide when just showing color.

INFLORESCENCE

Blooming habit: Continuous, upright, floriferous blooming; double flowers.
Borne: Florets on pedicel, pedicel on peduncle; 4.0–6.5 cm above foliage.
Open florets:
*Size fully open bloom.*—Umbel: 4.5–5.0 cm across. Floret: 1.5–2.5 cm across.
Form: Ruffled, slightly cupped.
Color:
*Top of petal.*—Red Group 55A at outer edge fading to Red Group 55B and then 55D. White at base of petal.

Slightly darker veining present. Upper petals have a larger white area with pink veins.

*Bottom of petal.*—Red-Purple Group 62A.

*Eye.*—White.

*Petals.*—Number: 7–9. Shape: Obovate, margin entire; separate, not united, flat to slightly cupped.

Texture and appearance: Velvety, highly reflective; appears from a distance as bright candy pink florets which fade to a pale pink with white at centers, with medium green foliage exhibiting a slightly darker zone.

Petaloids:

*Quantity.*—2.

*Shape.*—Twisted, irregular.

*Color.*—Top: Red Group 55B. Bottom: Red-Purple Group 62A.

Pedicel:

*Length.*—2.4–3.0 cm.

*Color.*—Yellow-Green Group 144B with Greyed-Purple Group 184B.

*Texture.*—Pubescent.

Peduncle:

*Length.*—16.0–17.5 cm.

*Color.*—Yellow-Green Group 144A.

*Texture.*—Pubescent.

Disease resistance: Not known.

Lasting quality: Heat tolerant; bloom is very quick to recover after wet conditions. Duration of bloom is 5–8 days, depending upon climate. Blooming period is 2 weeks after planting rooted cutting to first frost.

REPRODUCTIVE ORGANS

Stamens:

*Number.*—3–4 per flower.

*Anthers.*—1.0–2.0 mm long.

*Filaments.*—Length: 5.0–7.0 mm. Color: White with pink tips.

*Pollen color.*—Golden orange.

Pistils:

*Number.*—1; 5–6 parted.

*Length.*—7.0–8.0 mm.

*Stigma color.*—Pink.

Style:

*Length.*—3.0 mm.

*Ovaries.*—Pale green; pubescent; superior; 5.0 mm long.

Sepals:

*Number.*—5.

*Length.*—8–10 mm.

*Width.*—2–4 mm.

*Color.*—Yellow-Green Group 144A.

Fruit: Some fruit observed.

Seeds: None observed.

GENERAL CHARACTERISTICS

'Sophia' presents an improved floret form, better leaf form and color, and a more uniform habit than the current variety 'Marilyn', U.S. Plant Pat. No. 7,247. Cutting production and rooting speed are similar to the current market variety 'Elizabeth', U.S. Plant Pat. No. 8,192. This variety creates a uniform mound form with clean pink flowers which can be used in hanging baskets, containers or ground beds. 'Sophia' has been trialed both indoors and outdoors successfully during the springs and summers of 1995 and 1998 under a wide range of weather conditions. 'Sophia' has no distinguishing fragrance. 'Sophia' produces a root cutting in 3–4 weeks.

I claim:

1. A new and distinct cultivar of geranium plant named 'Sophia' as described and illustrated herein.

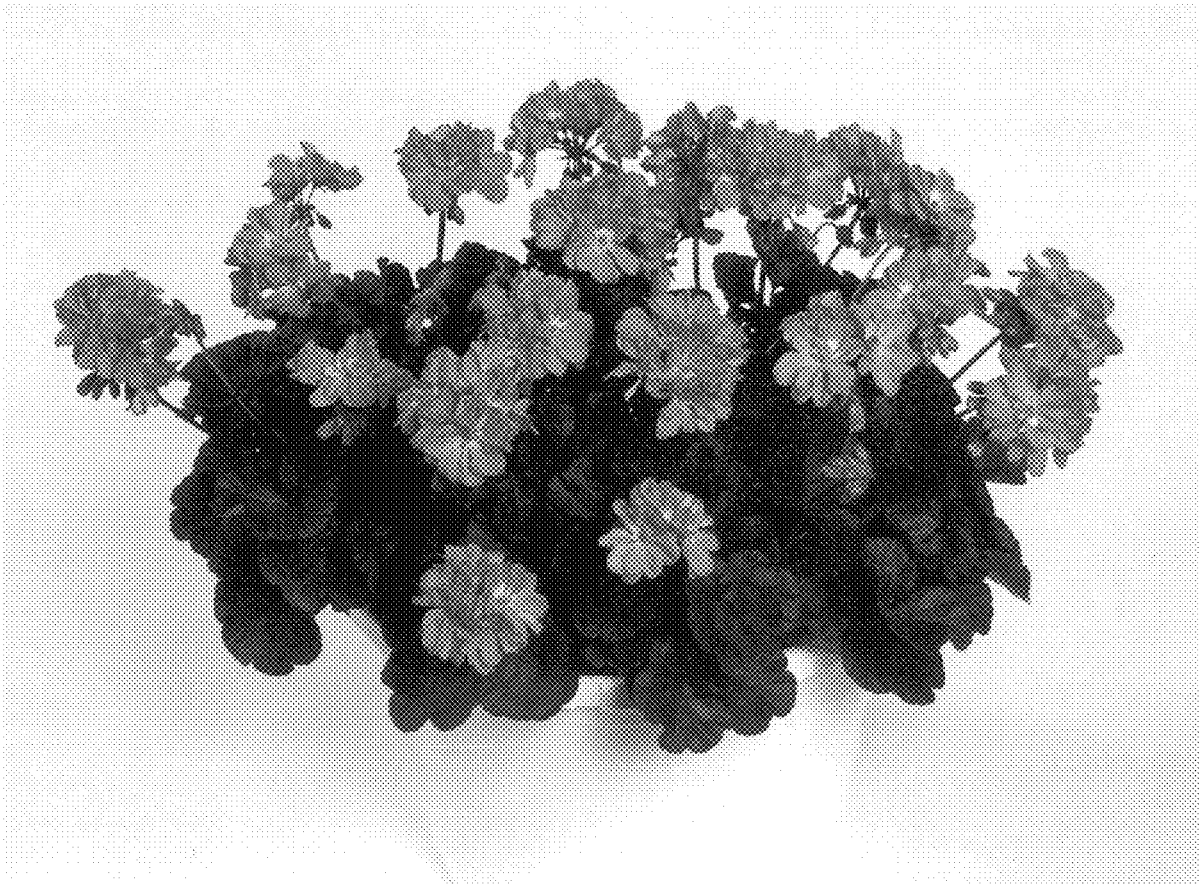

* * * * *